US005957925A

United States Patent [19]

Cook et al.

[11] Patent Number: 5,957,925

[45] Date of Patent: Sep. 28, 1999

[54] ORTHOPAEDIC MILLING INSTRUMENT

[75] Inventors: Kevin S. Cook, Warsaw; Stephen Rozow, III, Milford, both of Ind.

[73] Assignee: Bristol-Myers Squibb Co., New York, N.Y.

[21] Appl. No.: 09/081,892

[22] Filed: May 20, 1998

[51] Int. Cl.$^{6}$ .......................... A61B 17/00; A61B 17/14; A61F 5/00

[52] U.S. Cl. .................................................. 606/87; 606/79

[58] Field of Search .................................. 606/79, 80, 86, 606/87, 89, 99

[56] References Cited

U.S. PATENT DOCUMENTS

| | | | |
|---|---|---|---|
| 4,678,471 | 7/1987 | Noble et al. | 623/16 |
| 4,738,256 | 4/1988 | Freeman et al. | 128/92 |
| 4,777,942 | 10/1988 | Frey et al. | 128/92 VJ |
| 4,790,852 | 12/1988 | Noiles | 623/18 |
| 4,809,689 | 3/1989 | Anapliotis | 128/92 |
| 4,834,080 | 5/1989 | Brown | 128/92 |
| 5,047,033 | 9/1991 | Fallin | 606/87 |
| 5,108,453 | 4/1992 | Kotz et al. | 623/23 |
| 5,133,766 | 7/1992 | Halpern | 623/23 |
| 5,342,363 | 8/1994 | Richelsoph | 606/79 |
| 5,342,366 | 8/1994 | Whiteside et al. | 606/86 |
| 5,387,218 | 2/1995 | Meswania | 606/80 |
| 5,403,320 | 4/1995 | Luman et al. | 606/89 |
| 5,468,243 | 11/1995 | Halpern | 606/80 |
| 5,496,324 | 3/1996 | Barnes | 606/79 |
| 5,534,005 | 7/1996 | Tokish, Jr. et al. | 606/80 |
| 5,540,694 | 7/1996 | DeCarlo, Jr. et al. | 606/80 |
| 5,607,431 | 3/1997 | Dudasik et al. | 606/80 |

FOREIGN PATENT DOCUMENTS

| | | | |
|---|---|---|---|
| 0 496 636 A1 | 7/1992 | European Pat. Off. | A61F 2/46 |

*Primary Examiner*—Michael Buiz
*Assistant Examiner*—Vy Q. Bui
*Attorney, Agent, or Firm*—Cary R. Reeves

[57] ABSTRACT

A milling instrument for use in orthopaedic surgery includes an elongate stem for insertion into a prepared intramedullary canal of a bone. A pivotable mill includes a base connected to the stem and a cutting head pivotally connected to the base about a pivot axis. The cutting head has an axis of rotation and is rotatable about the axis of rotation. The cutting head has a first abutment surface positioned relative to the pivot axis and the base has a second abutment surface positioned relative to the pivot axis. The first abutment surface and the second abutment surface abut each other upon pivoting of the cutting head relative to the base at a predetermined angle and thereby limit the pivoting therebetween.

12 Claims, 3 Drawing Sheets

ORTHOPAEDIC MILLING INSTRUMENT

BACKGROUND OF THE INVENTION

1. Field of the invention

The present invention relates to instrumentation used in orthopaedic surgery, and, more particularly, to instrumentation used to prepare bone for receiving a prosthetic implant.

2. Description of the related art

In an orthopaedic surgery to replace part or all of a patient's joint with a prosthetic implant, a portion of the implant receiving bone is prepared to closely match the mating surfaces of the implant. During an orthopaedic surgery to replace a hip joint, the proximal end of the femur is prepared to accommodate a femoral hip prosthesis and the pelvic bone is prepared to accommodate an acetabular cup.

It is known to use an orthopaedic milling instrument to form the end of a bone to receive an orthopaedic implant. One or more guides or templates are typically attached to the end of the bone using screws, fasteners or the like. A milling cutter having a plurality of cutting teeth is rotatably driven to shape the end of the bone, and is guided using the guides or templates. Attaching the guides or templates to the end of the bone to guide the cutting head requires additional steps during the surgery, with resultant additional time required.

What is needed in the art is an orthopaedic milling instrument which accurately shapes the end of a bone for receiving a prosthetic implant and does not require additional guides or templates to guide and/or limit the cutting action of the cutting head.

SUMMARY OF THE INVENTION

The present invention provides an orthopaedic milling instrument with a pivotable mill having a base insertable into an intramedullary canal and a cutting head which is pivotally connected to the base and movable in a plane between abutting surfaces which limit the pivotal movement.

The invention comprises, in one form thereof, a milling instrument for use in orthopaedic surgery, including an elongated stem for insertion into a prepared intramedullary canal of a bone. A pivotable mill includes a base connected to the stem and a cutting head pivotally connected to the base about a pivot axis. The cutting head has an axis of rotation and is rotatable about the axis of rotation. The cutting head has a first abutment surface positioned relative to the pivot axis and the base has a second abutment surface positioned relative to the pivot axis. The first abutment surface and the second abutment surface abut each other upon pivoting of the cutting head relative to the base at a predetermined angle and thereby limit the pivoting therebetween.

An advantage of the present invention is that guides and/or templates are not needed to guide the cutting head of the orthopaedic milling instrument.

Another advantage is that the cutting head is only movable in a single plane relative to the base, thereby defining a precise cutting path through the bone.

Yet another advantage is that the shape, size and/or location of the abutment surfaces may be varied to a particular application, thereby providing flexibility in the design of the milling instrument.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The examples set out herein illustrate one preferred embodiment of the invention, in one form, and such examples are not to be construed as limiting the scope of the invention in any manner.

DETAILED DESCRIPTION OF THE INVENTION

Figure 1:
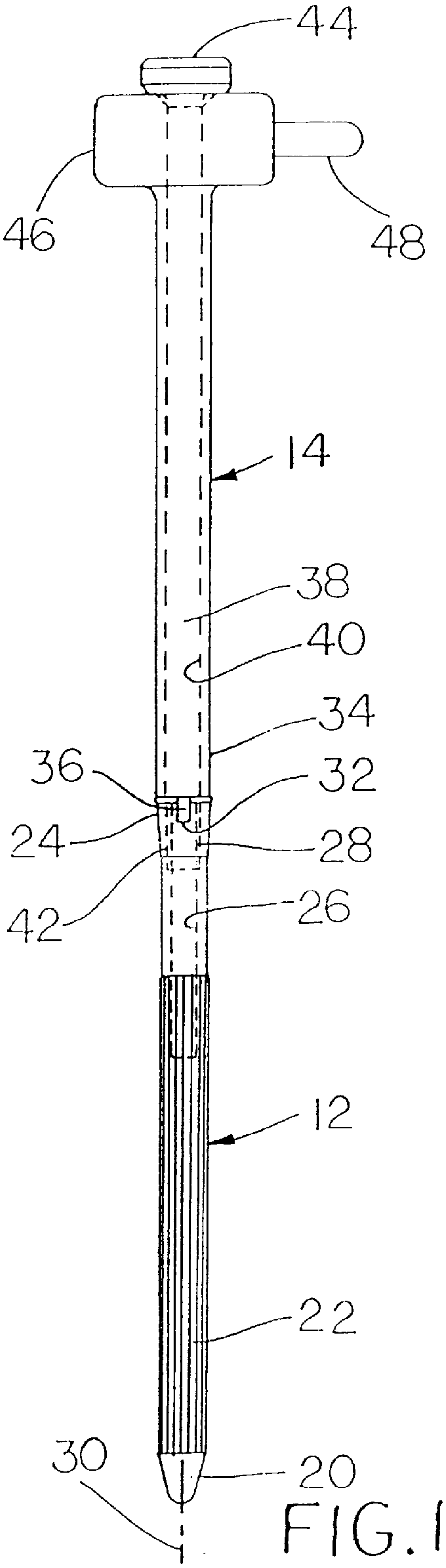
FIG. 1 is a plan view of an orthopaedic assembly of the present invention, including an embodiment of an inserter/extractor coupled with a stem.
Figure 2:
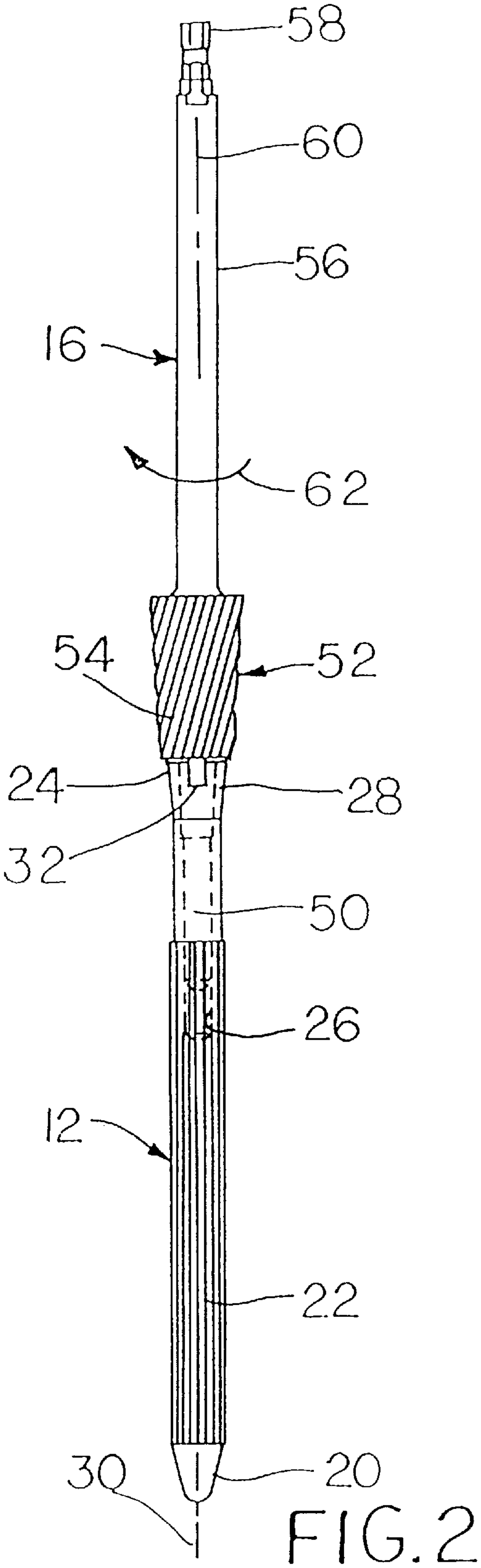
FIG. 2 is a plan view of an orthopaedic assembly of the present invention, including the stem of FIG. 1 and an embodiment of a rigid mill.
Figure 3:
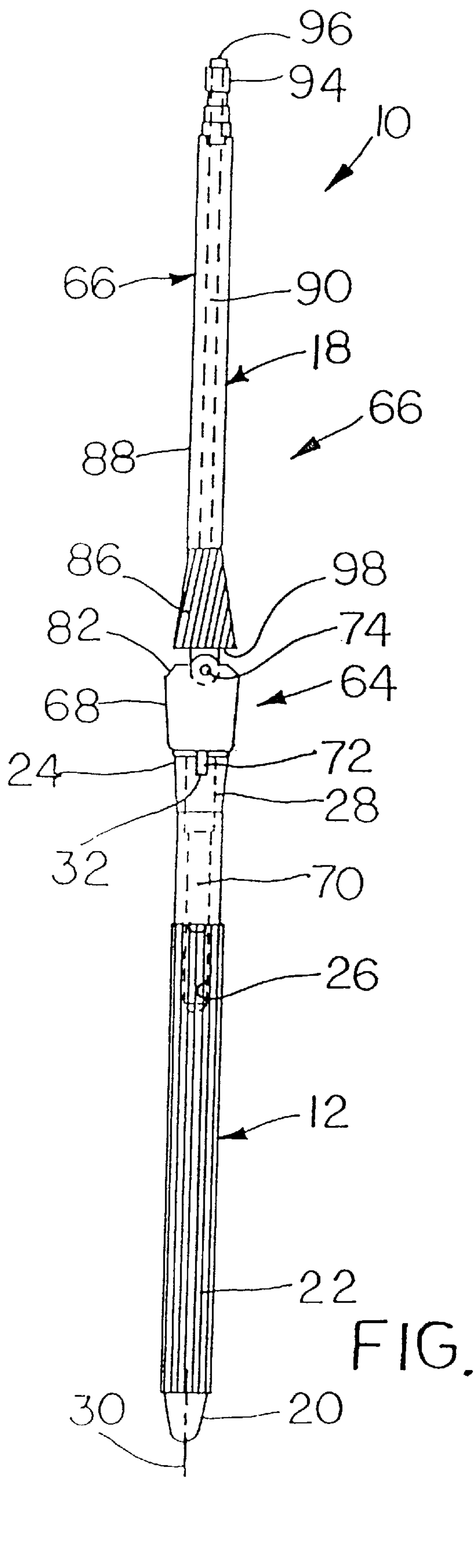
FIG. 3 is a plan view of an orthopaedic assembly of the present invention, including the stem of FIG. 1 and an embodiment of a pivotable mill of the present invention.

Referring now to the drawings, and more particularly to FIGS. 1–3, there is shown an orthopaedic assembly including an embodiment of an orthopaedic milling instrument 10 of the present invention. In the embodiment shown, the orthopaedic assembly is used to prepare the proximal end of a femur for receiving a femoral hip implant; however, the orthopaedic assembly may be used with other bones other than a femur. An elongate stem 12 is common to the orthopaedic assembly shown in each of FIGS. 1–3. A stem inserter/extractor 14 is coupled with stem 12 in FIG. 1; a rigid mill 16 is coupled with stem 12 in FIG. 2; and a pivotable mill 18 is coupled with stem 12 in FIG. 3.

Stem 12 is configured for insertion into a prepared intramedullary (IM) canal of a bone (not shown). Stem 12 includes a rounded end 20 and a plurality of external splines 22 which frictionally engage the sidewall of a prepared IM canal and prevent relative rotation with the bone. An open end 24 opposite rounded end 20 includes a longitudinally extending opening 26 with an internally threaded portion 28 positioned adjacent open end 24. Longitudinally extending opening 26 is positioned generally concentrically about a longitudinal axis 30. A keying arrangement in the form of a pair of notches 32 extends longitudinally from open end 24 on opposite sides of opening 26.

Inserter/extractor 14 includes an end 34 with a pair of projections 36 which are received within respective notches 32 of stem 12. A rod 38 extending through an internal, longitudinal bore 40 includes an externally threaded portion 42 which mates with internally threaded portion 28 of stem 12. A knob 44 opposite externally threaded portion 42 allows the threaded engagement between externally threaded portion 42 and internally threaded portion 28 to be tightened or loosened by the surgeon. A head 46 with an alignment handle 48 allows the surgeon to insert or extract stem 12 and align stem 12 relative to an anatomical landmark. When stem 12 is positioned within the proximal end of a femur, open end 24 is typically initially placed beneath the proximal end of the femur.

Rigid mill 16 includes a pilot nose 50 which is sized to be received within opening 26 of stem 12 with a relatively small clearance distance, and extend past internally threaded portion 28. A cutting head 52 having a plurality of external cutting teeth 54 mills the end of the bone after stem 12 is inserted therein. In the embodiment shown, cutting head 52 has a slight frustroconical shape which is used to mill a corresponding opening in the end of the bone. A stem 56 extending from cutting head 52 includes a drive head 58 which is connected with a suitable source of rotational power (not shown) for rotatably driving rigid mill 16 about a longitudinal axis 60, as indicated by arrow 62.

Figure 4:
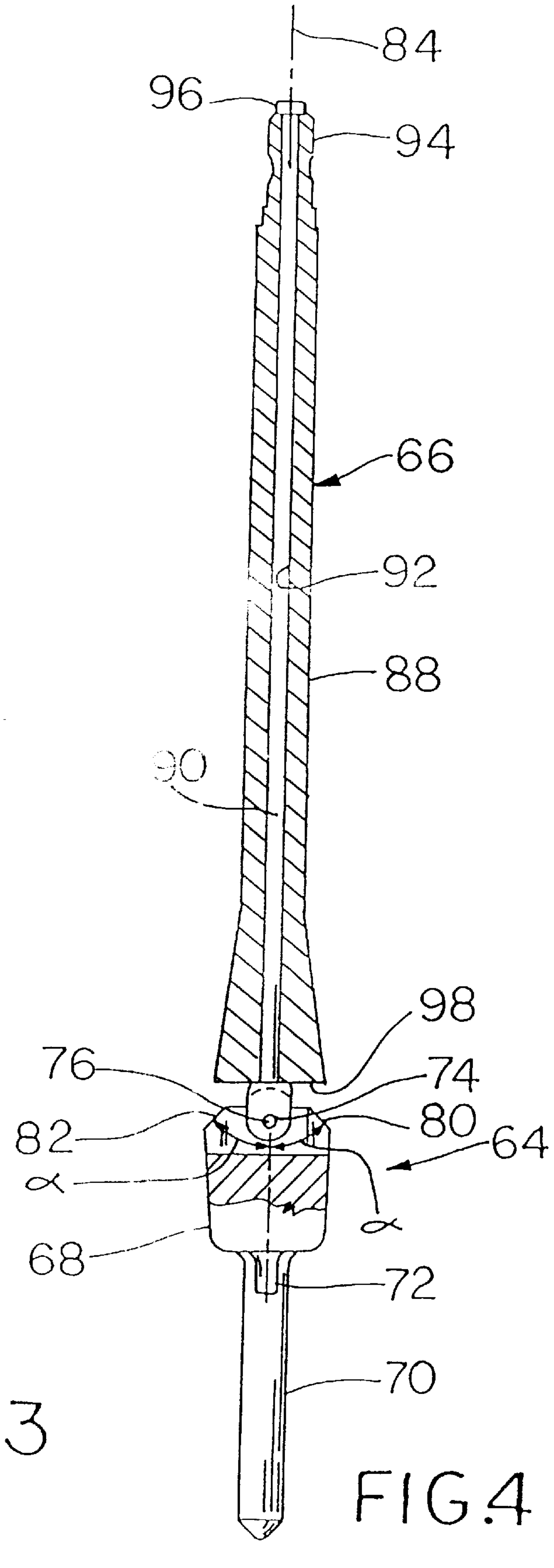
FIG. 4 is a partially sectioned, plan view of the pivotable mill of FIG. 3.
Figure 5:
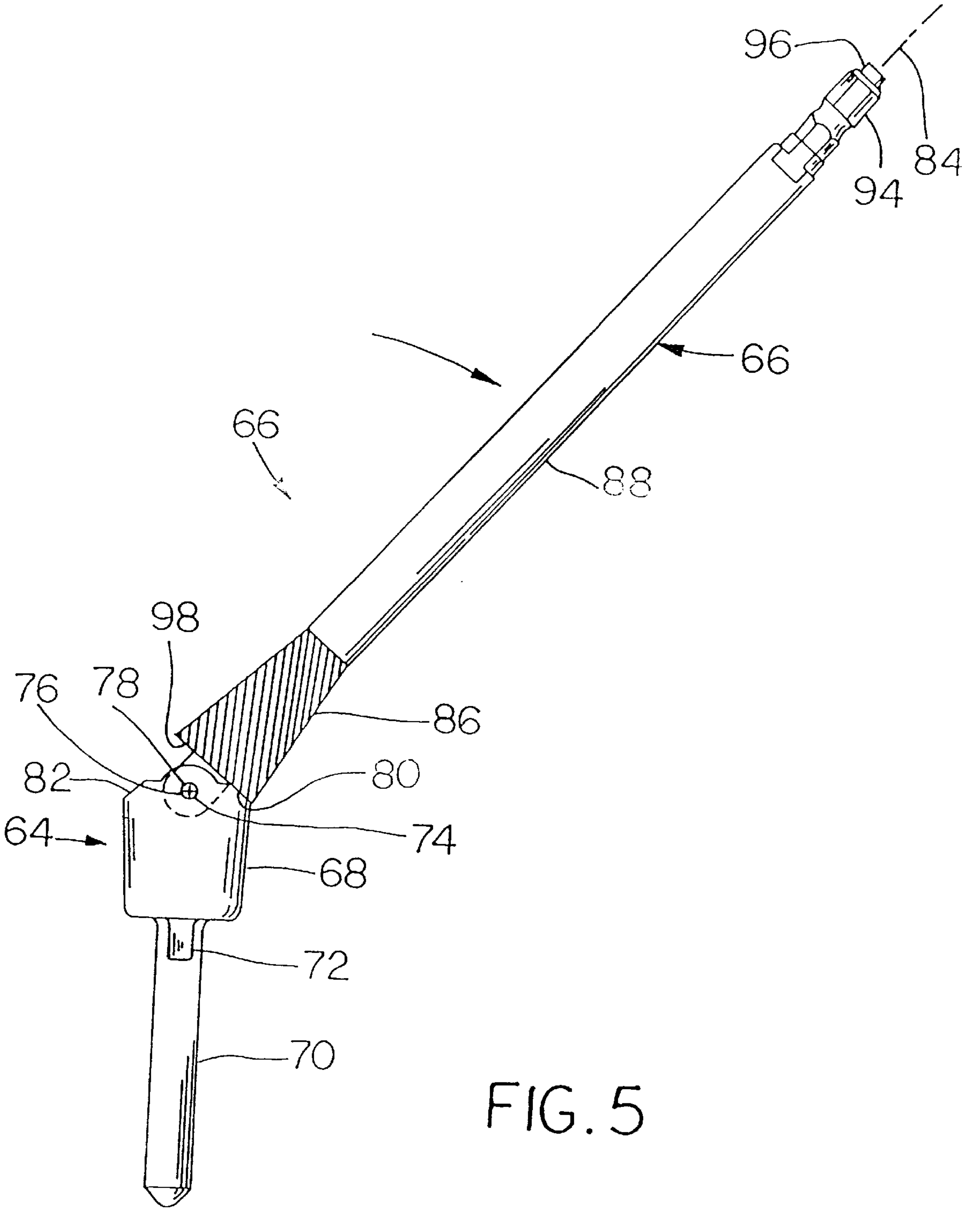
FIG. 5 is a plan view of the pivotable mill of FIGS. 3 and 4, with the cutting head pivoted relative to the base.

Pivotable mill 18, shown in FIGS. 3–5, includes a base 64 and cutting head 66. Base 64 has an enlarged end 68 and a pilot nose 70 extending therefrom and connected therewith. Pilot nose 70 is sized to be received within opening 26 of stem 12 with a relatively small clearance, and to extend past internally threaded portion 28. A keying arrangement in the form of a pair of projections 72 are positioned on opposite sides of pilot nose 70 and extend from each of enlarged end 68 and pilot nose 70. Projections 72 are received within and mate with notches 32 in open end 24 of stem 12 to prevent relative rotation between base 64 and stem 12.

Enlarged end 68 also includes an opening 74 and a pivot pin 76 disposed therein. Pivot pin 76 pivotally connects base 64 with cutting head 66, and defines a pivot axis 78. A pair of abutment surfaces 80 and 82 are positioned on generally opposite sides of pivot axis 78. Abutment surfaces 80 and 82 engage cutting head 66, and limit relative rotational movement between cutting head 66 and base 64 in respective opposite rotational directions about pivot axis 78. In the embodiment shown, abutment surfaces 80 and 82 are generally flat surfaces, however, it will be appreciated that abutment surfaces 80 and 82 may have any desired shape as long as they functionally limit the pivotal movement of cutting head 66. When pivoted in the opposite rotational directions between abutment surfaces 80 and 82, cutting head 66 is movable in a plane extending between the predetermined angles $\alpha$ and $\alpha'$. The plane of movement is substantially perpendicular to pivot axis 78. When cutting head 66 is at a maximum rotational position limited by abutment surface 80 or 82, the corresponding abutment surface 80 or 82 is disposed substantially perpendicular to an axis of rotation 84 of cutting head 66.

Cutting head 66 includes a plurality of cutting teeth 86 and a stem 88 which are carried and rotatable relative to an internal pin 90. More particularly, cutting teeth 86 are rigidly connected with stem 88. In the embodiment shown, cutting teeth 86 define a milling head with a generally frustroconical shape. The frustroconical shape of cutting teeth 86 shown in the drawings corresponds to the general shape of a metaphysial medial surface of a femoral hip prothesis. An elongate bore 92 extending through each of stem 88 and cutting teeth 86 and is sized to receive internal pin 90 therein. Stem 88 includes a drive head 94 at an end thereof which is adapted to be coupled with an external rotatable drive source (not shown) for driving each of stem 88 and cutting teeth 86 about pin 90. Pin 90 includes an enlarged head 96 which maintains the longitudinal position of stem 88 and cutting teeth 86 while still allowing free rotation thereabout.

Cutting teeth 86 include an end 98 which defines an abutment surface for engaging either of abutment surface 80 or 82 and thereby limiting the pivoting action between cutting head 66 and base 64. The abutment surface defined by end 98 is disposed substantially perpendicular to axis of rotation 84 in the embodiment shown, but need not necessarily be disposed at a perpendicular relationship.

In the embodiment shown, end 98 defines the abutment surface for engaging either of abutment surface 80 or 82. However, it will also be appreciated that internal pin 90 may also be formed with a surface defining an abutment surface for engaging either of abutment surface 80 or 82.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A milling instrument for use in orthopaedic surgery, comprising:

an elongate stem for insertion into a prepared intramedullary canal of a bone; and a pivotable mill including a base connected to said stem and a cutting head pivotally connected to said base about a pivot axis, said cutting head having an axis of rotation and being rotatable about said axis of rotation, said cutting head having a first abutment surface positioned relative to said pivot axis and said base having a second abutment surface positioned relative to said pivot axis, said first abutment surface and said second abutment surface abutting each other upon pivoting of said cutting head relative to said base at a predetermined angle and thereby limiting said pivoting therebetween.

2. The orthopaedic milling instrument of claim 1, wherein said cutting head includes an internal pin defining said axis of rotation and a plurality of cutting teeth rotatable about said internal pin.

3. The orthopaedic milling instrument of claim 2, wherein said first abutment surface is disposed substantially perpendicular to said axis of rotation.

4. The orthopaedic milling instrument of claim 1, wherein said base has a third abutment surface positioned relative to said pivot axis, said first abutment surface and said third abutment surface abutting each other upon pivoting of said cutting head relative to said base at a second predetermined angle and thereby limiting said pivoting therebetween.

5. The orthopaedic milling instrument of claim 1, wherein said second abutment surface is disposed substantially perpendicular to said axis of rotation when said cutting head is at said predetermined angle.

6. The orthopaedic milling instrument of claim 1, wherein said stem has a longitudinal axis and a longitudinally extending opening, and wherein said base has a pilot nose positioned within said longitudinally extending opening.

7. The orthopaedic milling instrument of claim 6, wherein said stem includes a first keying arrangement and said base includes a second keying arrangement, said first keying arrangement and said second keying arrangement mating with each other and positioning said base relative to said stem.

8. The orthopaedic milling instrument of claim 7, wherein said first keying arrangement comprises a plurality of notches and said second keying arrangement comprises a plurality of mating projections.

9. The orthopaedic milling instrument of claim 1, wherein said base is removably connected to said stem.

10. The orthopaedic milling instrument of claim 1, wherein said pivot axis defines a means for allowing pivotal movement of said cutting head in a single plane substantially perpendicular to said pivot axis.

11. The orthopaedic milling instrument of claim 1, wherein said axis of rotation is substantially perpendicular to said pivot axis.

12. The orthopaedic milling instrument of claim 1, wherein said first abutment surface is positioned at an end of said cutting head adjacent said pivot axis and said second abutment surface is positioned at an end of said base adjacent said pivot axis.

* * * * *